United States Patent [19]

Zerpner et al.

[11] Patent Number: 4,681,961
[45] Date of Patent: Jul. 21, 1987

[54] ADHESION PROMOTERS FOR THE PRODUCTION OF VOLCANIZATES HAVING A FAVORABLE FILLER/ELASTOMER BOND

[75] Inventors: Dieter Zerpner; Roland Streck; Horst G. Haag, all of Marl, Fed. Rep. of Germany

[73] Assignee: Huels Aktiengesellschaft, Marl, Fed. Rep. of Germany

[21] Appl. No.: 827,695

[22] Filed: Feb. 10, 1986

[30] Foreign Application Priority Data

Feb. 8, 1985 [DE] Fed. Rep. of Germany ....... 3504241
Aug. 14, 1985 [DE] Fed. Rep. of Germany ....... 3529109

[51] Int. Cl.⁴ ............................. C07F 7/08; C07F 7/18
[52] U.S. Cl. .................................... 556/428; 523/216
[58] Field of Search .......................................... 556/428

[56] References Cited

U.S. PATENT DOCUMENTS

| | | | |
|---|---|---|---|
| 3,530,160 | 9/1970 | Gardner et al. | 556/428 X |
| 3,555,067 | 1/1971 | Le Grow | 556/428 X |
| 3,842,111 | 10/1974 | Meyer-Simon et al. | 556/428 |
| 3,873,489 | 3/1975 | Thurn et al. | 556/428 X |
| 3,946,059 | 3/1976 | Janssen et al. | 556/428 |
| 3,978,103 | 8/1976 | Meyer-Simon et al. | 556/428 |
| 3,997,581 | 12/1976 | Pletka et al. | 556/428 X |
| 4,072,701 | 2/1978 | Pletka et al. | 556/428 X |
| 4,125,552 | 11/1978 | Speier | 556/428 |
| 4,129,585 | 12/1978 | Buder et al. | 556/428 |

Primary Examiner—Paul F. Shaver
Attorney, Agent, or Firm—Millen & White

[57] ABSTRACT

Novel adhesion promoters having, on the one hand, groups capable of forming a stable chemical bond with the surface of silicic acids and silicates (siloxane bond) and, on the other hand, groups capable of forming, during vulcanization, a stable chemical bond with an elastomer (sulfur bridges) are provided. They are consequently suitable as adhesion promoters for the production of vulcanizates exhibiting a favorable filler/elastomer bond. They are oligosulfanes of the formula $$(RO)_3Si-Y-S_x-Y-Si(OR)_3$$

wherein R, Y and x are defined herein, or a mixture of an oligosulfane of this formula (main product) and of a structurally related, substantially dimeric condensation product, which is characterized by a siloxane bond (by-product).

7 Claims, No Drawings

ADHESION PROMOTERS FOR THE PRODUCTION OF VOLCANIZATES HAVING A FAVORABLE FILLER/ELASTOMER BOND

BACKGROUND OF THE INVENTION

The invention relates to adhesion promoters for the production of vulcanizates obtained from heat-vulcanizable compositions and exhibiting a favorable filler/elastomer bond.

Such compositions are characterized by the following features:

They comprise an active, reinforcing filler, an elastomer component, an effective amount of a vulcanizing agent, and conventional additives The filler comprises a highly disperse filler from the group of silicic acids, silicates and mixtures thereof, and optionally rubber carbon blacks.

The elastomer component consists of one or several olefinically unsaturated elastomers capable of vulcanization with the vulcanizing agent.

The vulcanizing agent is a vulcanization system containing sulfur or sulfur donors in combination with conventional accelerators.

Heat-vulcanizable compositions are generally obtained by means of a process characterized by the following features:

A basic mixture (preliminary batch) is prepared in the first stage by hot mixing of the components, except for the vulcanizing agent, at higher than 130° C. in a kneader.

In the second stage, the vulcanizing agent is admixed (warm mixing) at lower than 100° C., especially lower than/equal to 70° C., i.e. generally far below the initiating temperature of the vulcanizing agent, for example on a roll.

In order to achieve a favorable filler/elastomer bond in the vulcanizates, it has proved necessary to treat the silicic acids and silicates with adhesion promoters. These must exhibit, on the one hand, groups capable of forming a stable chemical bond with the filler surface (typically a siloxane bond). On the other hand, they must exhibit groups capable of forming, during vulcanization, a stable chemical bond with the elastomer component (sulfur bridges) Accordingly, these adhesion promoters make possible the manufacture of vulcanizates exhibiting a favorable filler/elastomer bond.

The adhesion promoter is normally admixed in the first process stage. It can also be added in the second process stage prior to addition of the vulcanizing agent.

A conventional adhesion promoter is gamma-mercaptopropyltriethoxysilane. One disadvantage of said promoter resides in its volatility and unpleasant odor in handling. Another disadvantage is the premature occurrence of vulcanization, which may result in an impairment of flow characteristics and even in scorch, during processing of vulcanizable compositions containing a filler treated with this adhesion promoter.

Therefore, the practice has been adopted of using adhesion promoters overcoming these disadvantages characterized by the following formula:

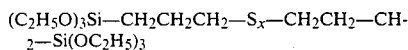

$(C_2H_5O)_3Si-CH_2CH_2CH_2-S_x-CH_2CH_2-CH_2-Si(OC_2H_5)_3$ wherein x is the number of S atoms in the individual compounds. The adhesion promoter is an oligosulfane (oligosulfide) which is characterized by a value V which is the number of S atoms, based on two Si atoms, as determined by elementary analyses (German Patent No. 2,712,866). In a commercially available adhesion promoter, V is approximately 4 (a "tetrasulfane").

Vulcanizable compositions obtained with the state of the art adhesion promoters show, in individual cases, a significant reduction in vulcanizing speed as compared with a vulcanizable composition obtained without an adhesion promoter.

SUMMARY OF THE INVENTION

It is an object of the invention to provide adhesion promoters overcoming or ameliorating such drawbacks of the prior art.

It is an additional object to provide adhesion promoters that do not give rise to unpleasant odors during handling, and in which no or little scorching occurs in the further processing of the vulcanizable composition.

It is a still further object to provide adhesion promoters that satisfy the useage requirements posed under practical conditions, particularly enabling production of vulcanizates with favorable filler/elastomer bonds without significant reduction of speed of vulcanization as compared to compositions obtained without adhesion promoters.

Upon further study of the specification and appended claims, further objects and advantages of this invention will become apparent to those skilled in the art.

These objects have been attained by providing an oligosulfane of the general Formula I $$(RO)_3Si-Y-S_x-Y-Si(OR)_3 \qquad (I)$$

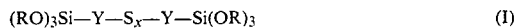

wherein R is methyl or ethyl, which residues R can be identical or different, x is the number of S atoms in the individual compounds and Y is

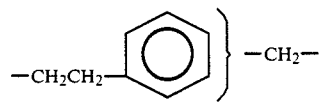

or

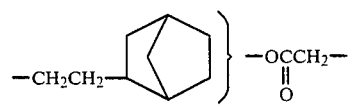

wherein the free ethylene linkage in each case is bonded to silicon and wherein the symbol} refers to substitution at either of the two encompassed positions in the individual compounds and in each case indicates a mixture of isomers; the oligosulfane being characterized by a value V of 2-6, preferably 2.5-5, most preferably 3-5, which is the number of S atoms, based on two Si atoms, as determined by elementary analyses.

Corresponding oligosulfanes of the general Formula I are:

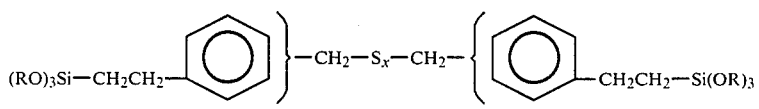

Bis[(beta-trialkoxysilylethyl)benzyl]oligosulfane; (I.1)

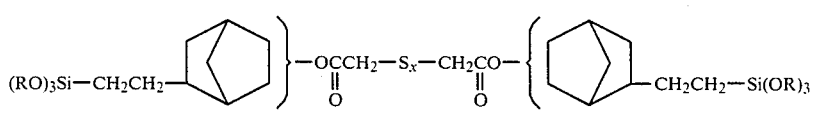

Oligosulfanediacetic acid bis[5-(beta-trialkoxysilylethyl) norborn-2(3)-yl]ester. (I.2)

These objects have been additionally attained by providing a mixture of oligosulfanes consisting of an oligosulfane of the general Formula I

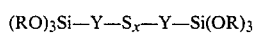

wherein R is methyl or ethyl, which residues R can be identical or different, x is the number of S atoms in the individual compounds and Y is

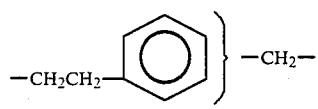

or

wherein the free ethylene linkage in each case is bonded to silicon and wherein the symbol } refers to substitution at either of the two encompassed prositions in the individual compounds and in each case indicates a mixture of isomers (main product, >50% by weight); and of a structurally related, substantially dimeric condensation product, which is characterized by a siloxane bond (by-product) and which may be characterized by the formula

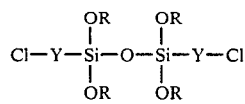

wherein R, Y and x have the meanings given above; the mixture being characterized by a value V of 2-6, preferably 2.5-5, most preferably 3-5, which is the number of S atoms, based on two Si atoms, as determined by elementary analyses;

the mixture being obtainable by a process comprising:

a.1 reacting, in the first stage, a compound of general Formula II $$Cl_3Si-Y-Cl \qquad (II)$$

with methanol and/or ethanol (alcoholysis);

a.2 the reaction product being a mixture of a compound of general Formula III $$(RO)_3Si-Y-Cl \qquad (III)$$

wherein R and Y have the meanings given above (main product) and of a structurally related, substantially dimeric condensation product, which is characterized by a siloxane bond (by-product) and which may be characterized by the formula

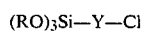

wherein R and Y have the meanings given above;

b.1 reacting, in the second stage, the thus-obtained crude reaction product under exclusion of air and moisture with a reagent prepared from sodium methylate and/or ethylate, finely divided sodium bisulfide, and finely divided sulfur in methanol and/or ethanol;

b.2 seperating the thus-formed sodium chloride and the solvent.

Corresponding compounds of the general Formula II are:

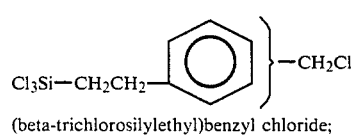

(beta-trichlorosilylethyl)benzyl chloride; (II.1)

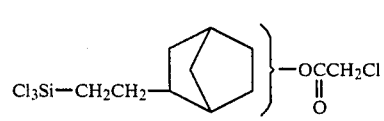

Chloroacetic acid [5-(beta-trichlorosilylethyl)-norborn-2(3)-yl] ester. (II.2)

Corresponding compounds of the general Formula III are:

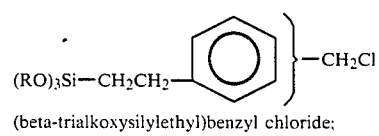

(beta-trialkoxysilylethyl)benzyl chloride; (III.1)

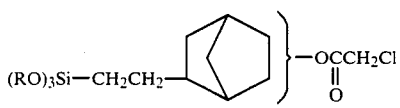

Chloroacetic acid
[5-(beta-trialkoxysilylethyl)-norborn-2(3-yl)] ester.

DETAILED DISCUSSION

Preparation of the (beta-trichlorosilylethyl)-benzyl chloride starting material of Formula II.1 (a mixture of isomers) used in step a.1 is known from German Patent No. 2,602,171, which disclosure is incorporated by reference herewith. Commercially available vinylbenzyl chloride, used for production of the starting material, is usually a mixture of the meta- and para-isomers.

The chloroacetic acid [5-(beta-trichlorosilylethyl)-norborn-2(3)-yl] ester starting material of Formula II.2 (also a mixture of isomers) used in step a.1 is novel. This compound can be prepared from 5-vinylnorborn-2-ene, obtainable commercially, in a two-stage process.

In the first stage, selective chemical addition of chloroacetic acid to the endocyclic double bond occurs with the formation of a mixture of chloroacetic acid[5-vinyl-norborn-2-yl] ester and of chloroacetic acid[5-vinylnorborn-3-yl] ester. This mixture of isomers is novel. Typically, the reaction is conducted at 120°–150 ° C. for 0.5–4 hours using 1–3 moles of chloroacetic acid per mole of 5-vinylnorborn-2-ene, preferably under a protective gas atmosphere in the presence of a polymerization inhibitor.

In the second stage, addition of trichlorosilane takes place to the double bond of the vinyl group, thus forming the ester of Formula II.2 (for details cf. German Patent No. 2,602,171 regarding the analogous addition of trichlorosilane to vinylbenzyl chloride).

The following reactions take place:

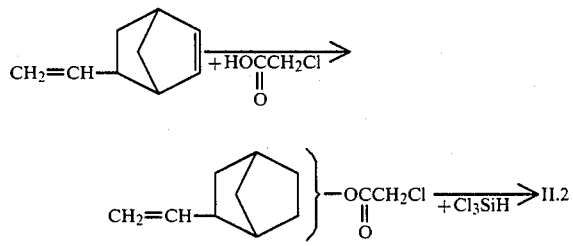

The mixture of chloroacetic acid [5-(beta-trialkoxysilylethyl)norborn-2(3)-yl] ester of general Formula III.2 (main product) and of the structurally related, substantially dimeric condensation product, which is characterized by a siloxane bond (by-product) is obtainable in accordance with feature a.1 by alcoholysis of the compound of Formula II.2 in the presence of a tertiary amine, e.g., triethyl amine, tri-n-butylamine, N-ethyl-, N,N-dicyclohexyl-amine, N-methylpiperidine, N,N-dimethylaniline, pyridine, at a temperature of <20 ° C., for a time of 0,3–2 hours using 8–30 moles of alcohol and 3–4 moles of tertiary amine per mole of II.2. The resultant aminohydrochloride and the solvent are separated (crude product).

As for the structure of the by-products described in feature a.2, e.g.,

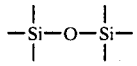

for the dimer, where the side chains on Si are OR and Y-based groups; see W. Noll, "Chemie und Technologie der Silikone" [Chemistry and Technology of Silicones], Chemie Publishers, pp. 71 et seq. (1968), which disclosure is incorporated herein.

The second process stage of feature b.1 is basically conventional (analogous process, German Patent No. 2,712,866, which disclosure is incorporated herewith). The separation stage b.2 is also fully conventional.

The bis[(Beta-trialkoxysilylethyl)benzyl]oligosulfane of general Formula I.1 and the oligosulfanediacetic acid bis[5-(beta-trialkoxysilylethyl)norborn-2(3)-yl]ester of general Formula I.2 can be obtained using this process comprising feature b.1 and feature b.2. Instead of the reaction product mixture obtained from feature a.2 in the first process stage, use is made in the second process stage (feature b.1) of separated (beta-trialkoxysilylethyl)benzyl chloride of general Formula III.1 or of separated chloroacetic acid [5-(beta-trialkoxysilylethyl)norborn-2(3)-yl] ester of general Formula III.2. These are in each case separated from the mixture (crude product) by conventional distillation under reduced pressure (usually <1 mbar).

The ester of general Formula III.2 can also be obtained directly by conventional chemical addition of a trialkoxysilane to the double bond of the vinyl group of the chloroacetic acid [5-vinylnorborn-2(3)-yl]ester.

Suitable non-limiting examples of elastomers for use in the improved vulcanizable compositions according to the invention are, for example, nitrile-butadiene rubber (NBR), natural rubber (NR), 1,4-cis-isoprene rubber (IR), polybutadiene rubber (BR), styrene-butadiene rubber (SBR), ethylene-propylene- unconjugated diene-rubber (EPDM), isoprene-isobutene rubber (IIR) and polyalkenylene elatomers, such as polypentenylene, polyoctenylene and polydodecenylene rubber.

The plasticizer oils customary in rubber technology can be utilized as additives in the vulcanizable compositions. Aromatic, aliphatic and naphthenic hydrocarbons are preferred. They can be added in the usual amounts.

Further customary auxiliary agents can also be incorporated in the usual quantities as the additive, such as, for example, zinc oxide, stearic acid, rosin acids, antiaging media, and ozone protection waxes.

The active reinforcing filler comprises at least 10, preferably at least 30% by weight of a highly disperse silicic acid and/or silicate coated (treated) with an adhesion promoter, the remainder (0–90, preferably 0–70% by weight) being a rubber carbon black. The silicic acids and silicates are treated with the adhesion promoter in the presence of the elastomer component (in situ).

The amount of total filler in the vulcanizable compositions usually is 30–150 parts by weight per hundred parts by weight of rubber.

The surface area of the silicic acid and silicate prior to treatment is usually 30–500, especially 35–300 m²/g, determined by nitrogen adsorption according to BET. The amount of adhesion promoter is usually 2–20, especially 4–15% by weight, based on the weight of untreated filler (silicic acids, silicates).

The adhesion promoter can be admixed in the first process stage described above. Normally, however, the adhesion promoter is admixed in the second process stage before adding the vulcanizing agent. It is also possible to admix a portion of the necessary amount of adhesion promoter, for example 4–80% by weight thereof, in the first stage, and the remainder in the second process stage.

Unless indicated otherwise herein, all details of the compositions and preparation of the heat vulcanizable compositions and vulcanizates, as well as the use of the adhesion promoters of this invention therein, are fully conventional, e.g., as discussed in ASTM D 3185, which disclosure is incorporated by reference herewith.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

In the preparation directions, percent (%) means percent by weight; M means the relative molecular weight and $\overline{M}n$ means the number-average, relative molecular weight. The molecular weights are determined be vapor pressure osmometry.

In the examples, parts (p) mean parts by weight. The comparative examples, vulcanizable compositions(compounds) and vulcanizates (test specimens) not in accordance with this invention are denoted by capital letters.

Preparation of Chloroacetic Acid [5-Vinylnorborn-2(3)-yl]Ester

Under dry nitrogen, 720 g of 5-vinylnorborn-2-ene (purity as per gas chromatography higher than/equal to 98%) and 842 g of chloroacetic acid are heated in a three-necked flask with internal thermometer, stirrer and reflux condenser with addition of 4.8 g of 2,2'-methylenebis(6-tert-butyl-4-methylphenol) to 140° C., thus initiating the slightly exothermic reaction. The temperature of the reaction mixture was maintained for another two hours at 140° C.; after cooling, the excess chloroacetic acid was separated by dissolution in water, and the organic phase was washed neutral with aqueous sodium bicarbonate solution and water. After drying over calcium chloride, distillation under vacuum yielded 928 g (72% of theory) of a colorless fluid ($n_D^{20}$:1.4951). The indicated structure (mixture of isomers) was confirmed by NMR and GC analyses.

Preparation of Chloroacetic Acid [5-(Beta-trimethoxysilylethyl)norborn-2(3)-yl]Ester (Formula III.2, R:—CH$_3$)

Under dry nitrogen, 214 g of chloroacetic acid [5-vinylnorborn-2(3)-yl]ester was heated to 80° C., with the addition of 400 mg of phenothiazine and a solution of 200 mg of hexachlorohydroplatinic acid in 10 cc of tetrahydrofuran, in a three-necked flask with internal thermometer, stirrer, reflux condenser and dropping funnel, and then 110 cc of trichlorosilane was added dropwise within 30 minutes, the temperature of the exothermic reaction being maintained at 80° C. by cooling. After all of the trichlorosilane had been added, the reaction mixture was maintained for another 1.5 hours at 80° C. Thereafter, readily volatile proportions were removed by vacuum distillation.

The thus-obtained reaction product (chloroacetic acid [5-(beta-trichlorosilylethyl)norborn-2(3)-yl] ester of Formula II.2) was added via a dropping funnel under dry nitrogen to a vigorously agitated mixture of 1 liter of methanol and 60 cc of triethylamine. The temperature of the batch was maintained between 10° and 15° C. by cooling. At the same time, another 478 cc of triethylamine was added dropwise so that addition of both liquids was finished simultaneously after about 30 minutes. The thus-precipitated salt (aminohydrochloride) was suctioned off and washed with dry toluene. The filtrate, after removing the methanol by distillation with a rotary evaporator, was combined with 400 cc of dry toluene, the precipitated salt was suctioned off, washed with toluene, and the filtrate freed of toluene, thus obtaining 299 g (89% of theory) of a crude product ($n_D^{20}$:1.4720; M:360) which yielded, after distillation at ca. 145° C./0,3 mbar, 265 g (79% of theroy) of a colorless fluid ($n_D^{20}$:1.4700; M:350). The indicated structure (mixture of isomers) was confirmed by NMR and GC analyses.

Preparation of Chloroacetic Acid [Beta(triethoxysilylethyl)norborn-2(3)-yl] Ester (Formula III.2,,-R:—C$_2$H$_5$)

The above directions were altered by replacing methanol by ethanol. The yield was 306 g (81% of theory) of a crude product ($n_D^{20}$:1.4649; M:420) which gave, after distillation at ca. 155° C./0,3 mbar, 254 g (67% of theory) of a colorless liquid ($n_D^{20}$:1.4628; M:390).

Production of the Adhesion Promoters of This Invention

Preparation of Bis[(beta-trimethoxysilylethyl)benzyl-]oligosulfane, Adhesion Promoter 1(Formula I.1,-R:—CH$_3$)

In an agitated reactor, 200 cc of dry methanol and then 4.8 g of sodium were provided under a protective atmosphere of dry nitrogen. To the thus-obtained sodium methylate solution was added a mixture of 11.7 g of finely divided sodium bisulfide and 20 g of finely divided sulfur. Gradually and under cooling, 110 g of (beta-trimethoxysilylethyl)benzyl chloride [Formula III.1, R:—CH$_3$, $n_D^{20}$:1.4976; M:290; obtained by distillation at ca. 125° C./0,3 mbar from the mixture of main product and a substantially dimeric by-product characterized by a siloxane bond and resulting from the reaction of (beta-trichlorosilylethyl)benzyl chloride of Formula II.1 (mixture of meta- and para-isomers) with methanol]was added to the resultant, orange-red reagent solution (reaction temperature:50°–60° C.). The reaction mixture was heated for 2 hours under reflux. The thus-precipitated sodium chloride was separated and washed with methanol. The combined filtrates were freed of methanol in a rotary evaporator under reduced pressure. Yield: 114 g of an orange-red, liquid reaction product ($n_D^{20}$:1.5708; $\overline{M}n$:600; 19.1% S; 10.1% Si; 3.3 S atoms/2 Si atoms). The above-indicated structure was confirmed by IR and NMR analyses.

Preparation of Bis[(beta-triethoxysilylethyl)benzyl-]oligosulfide, Adhesion Promoter 2(Formula I.1,-R:—C$_2$H$_5$)

The directions for producing adhesion promoter 1 were altered by using, in place of methanol, dry ethanol and, in place of the 110 g of (beta-trimethoxysilylethyl)-benzyl chloride, 127 g of (beta-triethoxysilylethyl)benzyl chloride (Formula III.1, R:—C$_2$H$_5$, $n_D^{20}$:1.4843; M:310; obtained by distillation at ca. 130° C./0,3 mbar form the mixture resulting from the reaction of (beta-trichlorosilylethyl)benzyl chloride of Formula II.1 with ethanol). Yield: 125 g of an orange-red, liquid reaction product ($n_D^{20}$:1.5436; $\overline{M}n$:720; 17.3% S; 8.08% Si; 3.75 S atoms per 2 Si atoms). The indicated structure was confirmed by IR and NMR analyses.

Preparation of a Mixture of Bis[(beta-trimethoxysilylethyl)benzyl]oligosulfane (main product of Formula I.1, R:—CH$_3$) and a substantially dimeric by-product, characterized by a siloxane bond, Adhesion Promoter 3

The directions for preparing adhesion promoter 1 were modified by using, instead of (beta-trimethoxysilylethyl)benzyl chloride of Formula III.1, R:—CH$_3$, the same amount of the crude mixture of (beta-trimethoxysilylethyl)benzyl chloride (main product) and a substantially dimeric by-product, which is characterized by a siloxane bond ($n_D^{20}$:1.5040; $\overline{M}n$:310) obtained by reaction of (beta-trichlorosilylethyl)benzyl chloride of Formula II.1 with methanol. Yield:110 g of an orange-red, liquid reaction product ($n_D^{20}$:1.5741; $\overline{M}n$:830; 20.4% S; 9.31% Si; 3.84 S atoms/2 Si atoms).

Preparation of Oligosulfanediacetic Acid Bis[5-(beta-trimethoxysilylethyl)norborn-2(3)-yl] Ester, Adhesion Promoter 4 (Formula I.2, R:—CH$_3$)

In an agitated reactor, 200 cc of dry methanol and then 4.8 g of sodium were provided under a protective atmosphere of dry nitrogen. To the thus-obtained sodium methylate solution was added a mixture of 11.7 g of finely divided sodium bisulfide and 20 g of finely divided sulfur. Gradually and under cooling, 135 g of chloroacetic acid [5-(beta-trimethoxysilylethyl)norborn-2(3)-yl] ester (Formula III.2, R:—CH$_3$) was added to the resultant, orange-red reagent solution (reaction temperature 50°-60° C.). The reaction mixture was heated under reflux for 2 hours. The thus-precipitated sodium chloride was separated and washed with methanol. The combined filtrates were freed of methanol in a rotary evaporator under reduced pressure. Yield:136 g of an orange-colored, liquid reaction product ($n_D^{20}$:1.5098; $\overline{M}n$:700; 13.9% S; 7.9% Si; 3.1 S atoms per 2 Si atoms). The indicated structure was confirmed by IR and NMR analyses.

Preparation of Oligosulfanediacetic Acid Bis[5-(beta-triethoxysilylethyl)norborn-2(3)-yl]Ester, Adhesion Promoter 5(Formula I.2,R:—C$_2$H$_5$)

The directions for producing adhesion promoter 4 were modified by employing, in place of methanol, dry ethanol and, in place of 135 g of chloroacetic acid [5-(beta-trimethoxysilylethyl)norborn-2(3)-yl]ester, 151 g of chloroacetic acid [5-(beta-triethoxysilylethyl)norborn-2(3)-yl] ester. Yield: 147 g of an orange-colored, liquid reaction product ($n_D^{20}$:1.5000; $\overline{m}n$ :790; 12.9% S; 7.35% Si; 3.1 S atoms/2 Si atoms). The indicated structure was confirmed by IR and NMR analyses.

Preparation of a Mixture of Oligosulfanediacetic Acid Bis[5-(beta-trimethoxysilylethyl)norborn-2(3)-yl] Ester (main product of Formula I.2, R:—CH$_3$) and a substantially dimeric by-product, characterized by a siloxane bond, Adhesion Promoter 6

The directions for producing adhesion promoter 4 were altered by using, instead of chloroacetic acid [5-(beta-trimethoxysilylethyl)norborn-2(3)-yl] ester of Formula III.2, R:—CH$_3$, the same amount of the crude mixture of chloroacetic acid [5-(beta-trimethoxysilylethyl)norborn-2(3)-yl] ester (main product) and a substantially dimeric by-product, which is characterized by a siloxane bond. Yield: 132 g of an orange-colored, liquid reaction product ($n_D^{20}$:1.5103; $\overline{M}n$:790; 14.1% S; 9.5% Si; 2.6 S atoms per 2 Si atoms).

Production of the Compounds

In an internal mixer, the basic mixtures were first produced in accordance with the formulations set out below. During this procedure, the temperature rose in each case to about 140° C. (first process stage). On a rolling mill, at about 50° C., the vulcanizing agent or initially the adhesion promoter and then the vulcanizing agent was and, respectively, were admixed thereto thereafter (second process stage).

EXAMPLE 1 (COMPOUND 1)

Formulation of the basic mixture (first process stage):

| | |
|---|---|
| NBR [weight ratio of basic monomers acrylonitrile/1,3-butadiene: 28/72; heat-polymerized product; Mooney viscosity (ML$_{1+4}$, 100° C., DIN 53 523): 65] | 100 p |
| Stearic acid | 2 p |
| Zinc oxide | 7 p |
| Highly disperse, precipitated silicic acid (surface area: 170 m$^2$/g, determined by nitrogen adsorption according to BET) | 60 p |
| Adhesion promoter 1 | 2 p |
| Commercially available dispersing agent | 5 p |
| Coumarone resin | 6 p |
| Dioctyl phthalate | 12 p |
| Vulcanizing Agent (Second Process Stage): | |
| Dibenzothiazyl disulfide | 1 p |
| Diphenylguanidine | 1 p |
| Tetramethylthiuram monosulfide | 0.8 p |
| Sulfur | 2.5 p |

EXAMPLE 2 (COMPOUND 2)

Example 1 was modified by admixing adhesion promoter 1, rather than in the first stage, in the second process stage, namely before the vulcanizing agent.

EXAMPLE 3 (COMPOUND 3)

Example 1 was modified by using adhesion promoter 4 in place of adhesion promoter 1.

EXAMPLE 4 (COMPOUND 4)

Example 2 was modified by using adhesion promoter 4 in place of adhesion promoter 1.

EXAMPLE A (COMPOUND A)

Example 1 was modified by using the adhesion promoter of the prior art (tetrasulfane) instead of adhesion promoter 1.

EXAMPLE B (COMPOUND B)

Example 2 was modified by using tetrasulfane in place of adhesion promoter 1.

EXAMPLE C (COMPOUND C, BLIND TEST)

Example 1 was modified by omitting adhesion promoter 1.

Testing the Vulcanizing Rate of the Compounds

The vulcanizing rate of the compounds was determined with a Zwick oscillatory elastometer at 160° C. and with a deformation amplitude of 1° and 3 oscillations per minute.

TABLE 1

| Compound (Process Stage in Which Adhesion Promoter Was Admixed) | Time [min] to Conversion During Vulcanization of | |
|---|---|---|
| | 10% ($t_{10}$) (*) | 90% ($t_{90}$) (*) |
| 1 (1st) Adhesion Promoter 1 | 2.1 | 6.1 |
| 2 (2nd) Adhesion Promoter 1 | 2.1 | 4.5 |
| 3 (1st) Adhesion Promoter 4 | 1.5 | 5.6 |
| 4 (2nd) Adhesion Promoter 4 | 1.4 | 6.3 |
| A (1st) Tetrasulfane | 2.0/2.2 | 11.3/9.5 |
| B (2nd) Tetrasulfane | 2.4/2.1 | 10.9/9.6 |
| C Blind test | 2.3/2.4 | 3.3/3.5 |

(*)The control values were obtained with compounds produced under conditions identical to those of the compounds forming the basis for the initial measurements.

Compounds 1–4 with adhesion promoters 1 and 4 of this invention exhibit a markedly higher vulcanizing rate than compounds A and B with the adhesion promoter of the prior art (tetrasulfane).

Similar results are obtained by using adhesion promoter 2, 3, 5 or 6, instead of adhesion promoter 1, in the preparation of the compounds.

Production and Testing of Vulcanized Test Specimens

In a press, test specimens 1–4 and A–C were made from compounds 1–4 and A–C at 160° C. (time [min]: 9, 7, 6, 9, 14/12, 14/13 and 6/6, respectively).

The specimens were characterized as indicated in Table 2 (thickness of the test specimens, cut in accordance with the standards: 4 mm).

TABLE 2

| Test Specimen | Usage Properties of Vulcanized Test Specimens | | | | | | |
|---|---|---|---|---|---|---|---|
| | 1 | 2 | 3 | 4 | A/() | B/() | C/(**) |
| Tensile strength (DIN 53 504) [MPa] | 9.6 | 9.9 | 12.4 | 13.4 | 10.0/10.4 | 9.6/10.9 | 8.0/10.0 |
| Elongation at break (DIN 53 504) [%] | 213 | 203 | 204 | 221 | 210/217 | 190/231 | 326/332 |
| Stress value at 200% elongation (DIN 53 504) [MPa] | 8.9 | 9.8 | 11.6 | 11.9 | 9.4/9.3 | 9.1 | 5.0/5.7 |
| Permanent elongation (intenal method, measurement after 1 min) [%] | 3 | 3 | 4 | 4 | 3/2 | 3/3 | 4/4 |
| Cut growth resistance according to Pohle (internal method) [N/mm] | 16 | 16 | 23 | 26 | 14/21 | 14/16 | 16/20 |
| Shore hardness A (DIN 53 505) | 70 | 70 | 66 | 66 | 70/66 | 70/67 | 65/64 |
| Rebound resilience (ISO IR 1767) [%] | 37 | 38 | 44 | 43 | 40/46 | 40/46 | 38/46 |
| Abrasion (DIN 53 516) [mm$^3$] | 132 | 127 | 133 | 124 | 137/160 | 130/154 | 188/200 |
| Compression set (DIN 53 517, Method B) [%](*) | 11 | 15 | 12 | 11 | 13/14 | 13/12 | 17/26 |

(*)After 22 hour storage at 70° C. in the compressed condition.
(**)The control data were obtained with vulcanized test specimens produced under conditions identical to those for the test specimens forming the basis for the initial measurements.

Test specimens 1 through 4 with adhesion promoter 1 or 4, respectively, exhibit test values which practically correspond to those of test specimens A and B with the adhesion promoter of the prior art (tetrasulfane), or which are even more favorable than these.

Similar results are achieved by using adhesion promoter 2, 3, 5 or 6, instead of adhesion promoter 1 or 4, respectively, in preparing compounds 1–4 on which test specimens 1–4 are based.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An oligosulfane mixture of the formula

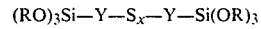

wherein R is methyl or ethyl, which residues R can be identical or different, x is the number of S atoms in the individual compounds and Y is

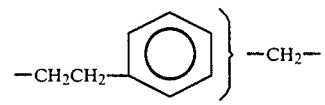

or

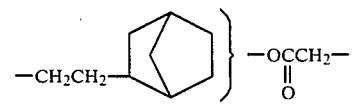

wherein the free ethylene linkage in each case is bonded to silicon and wherein the symbol } refers to substitution at either of the two encompassed positions in the individual compounds and in each case indicates a mixture of isomers;

the oligosulfane being characterized by a value V of 2–6 which is the number of S atoms, based on two Si atoms, as determined by elementary analyses.

2. A mixture of oligosulfanes consisting of an oligosulfane of the formula

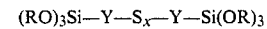

wherein R is methyl or ethyl, which residues R can be identical or different, x is the number of S atoms in the individual compounds an Y is

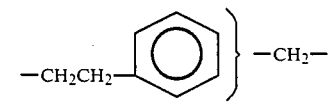

or

-continued

wherein the free ethylene linkage in each case is bonded to silicon and wherein the symbol } refers to substitution at either of the two encompassed positions in the individual compounds and in each case indicates a mixture of isomers (main product, >50% by weight);
and of a structurally related, substantially dimeric condensation product, which is characterized by a siloxane bond (by-product) and which may be characterized by the formula

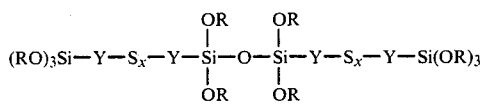

wherein R, Y and x have the meanings given above; the mixture being characterized by a value V of 2-6, which is the number of S atoms, based on two Si atoms, as determined by elementary analyses;
the mixture being obtainable by a process comprising:
a.1 reacting, in the first stage, a compound of formula

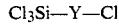

with methanol and/or ethanol (alcoholysis);
a.2 the reaction product being a mixture of a compound of formula

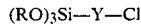

wherein R and Y have the meanings given above (main product) and of a structurally related, substantially dimeric condensation product, which is characterized by a siloxane bond (by-product) and which may be characterized by the formula

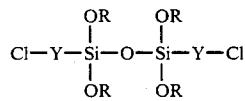

wherein R and Y have the meanings given above;
b.1 reacting, in the second stage, the thus-obtained crude reaction product under exclusion of air and moisture with a reagent prepared from sodium methylate and/or ethylate, finely divided sodium bisulfide, and finely divided sulfur in methanol and/or ethanol;
b.2 seperating the thus-formed sodium chloride and the solvent.

3. An oligosulfane of the formula

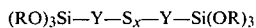

wherein each R independently is methyl or ethyl, x is 2-6, and Y is

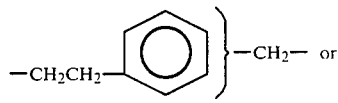

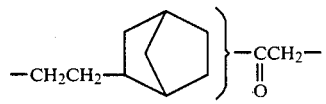

wherein the free ethylene linkage in each case is bonded to silicon and wherein the symbol } refers to attachment of —CH$_2$ at either of the encompassed positions.

4. An oligosulfane of claim 3 wherein x is 3-5.
5. An oligosulfane of claim 1, wherein V is 3-5.
6. An oligosulfane of claim 1, wherein V is 2.5-5.
7. A mixture of (a) oligosulfanes of the formula

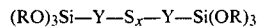

wherein R is independently methyl or ethyl, x is the number of S atoms in the individual compounds and Y is

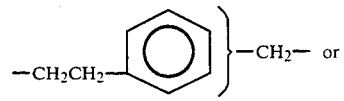

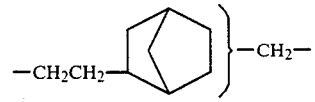

wherein the free ethylene linkage in each case is bonded to silicon and wherein the symbol } refers substitution at either of the two encompassed positions in the individual compounds and in each case indicates a mixture of isomers; and (b) a substantially dimeric condensation product, of the formula

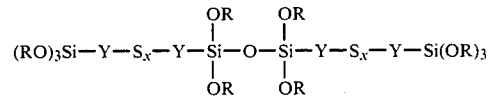

wherein R, Y and x independently have the meanings given above; and x has an average value of 2-6.

* * * * *

UNITED STATES PATENT AND TRADEMARK OFFICE
CERTIFICATE OF CORRECTION

PATENT NO. : 4,681,961

DATED : July 21, 1987

INVENTOR(S) : Dieter Zerpner et al

It is certified that error appears in the above-identified patent and that said Letters Patent is hereby corrected as shown below:

Title Page, [54], Title:

Reads: "ADHESION PROMOTERS FOR THE PRODUCTION OF VOLCANIZATES HAVING A FAVORABLE FILLER/ELASTOMER BOND"

should read: --ADHESION PROMOTERS FOR THE PRODUCTION OF VULCANIZATES HAVING A FAVORABLE FILLER/ELASTOMER BOND--

Signed and Sealed this

Third Day of November, 1987

Attest:

DONALD J. QUIGG

Attesting Officer

Commissioner of Patents and Trademarks